US009808267B2

(12) United States Patent
Smith et al.

(10) Patent No.: US 9,808,267 B2
(45) Date of Patent: Nov. 7, 2017

(54) TISSUE RESECTION DEVICE AND RELATED METHODS OF USE

(71) Applicant: Boston Scientific Scimed, Inc., Maple Grove, MN (US)

(72) Inventors: Paul Smith, Smithfield, RI (US); Naroun Suon, Lawrence, MA (US); Oscar R. Carrillo, Jr., Attleboro, MA (US); Samuel Raybin, Marlborough, MA (US); Barry Weitzner, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 532 days.

(21) Appl. No.: 13/906,528

(22) Filed: May 31, 2013

(65) Prior Publication Data

US 2013/0331855 A1 Dec. 12, 2013

Related U.S. Application Data

(60) Provisional application No. 61/658,700, filed on Jun. 12, 2012.

(51) Int. Cl.
*A61B 17/221* (2006.01)
*A61B 17/00* (2006.01)
*A61B 17/34* (2006.01)
*A61B 17/12* (2006.01)

(52) U.S. Cl.
CPC ...... *A61B 17/221* (2013.01); *A61B 17/00234* (2013.01); *A61B 17/12013* (2013.01); *A61B 2017/00269* (2013.01); *A61B 2017/00296* (2013.01); *A61B 2017/3445* (2013.01)

(58) Field of Classification Search
CPC ........ A61B 17/00234; A61B 17/12022; A61B 17/12013; A61B 2017/00296; A61B 2017/00292; A61B 2017/00269; A61B 2017/3445; A61B 17/221
USPC .................. 606/114, 130; 600/101, 107, 127
See application file for complete search history.

(56) References Cited

U.S. PATENT DOCUMENTS

| 4,747,661 | A | * | 5/1988 | Ohkuwa | A61B 1/00096 385/118 |
|---|---|---|---|---|---|
| 5,827,177 | A | * | 10/1998 | Oneda | A61B 1/018 600/121 |
| 6,338,345 | B1 | * | 1/2002 | Johnson | A61B 17/12036 128/897 |
| 7,507,200 | B2 | * | 3/2009 | Okada | A61B 1/012 600/104 |
| RE42,050 | E | * | 1/2011 | Richard | A61B 17/221 606/114 |
| 8,192,403 | B1 | * | 6/2012 | Pursley | A61M 25/01 600/585 |
| 2003/0040657 | A1 | * | 2/2003 | Yamaya | A61B 1/00039 600/107 |
| 2004/0082883 | A1 | * | 4/2004 | Kohno | A61B 1/00096 601/2 |

(Continued)

*Primary Examiner* — Jocelin Tanner
(74) *Attorney, Agent, or Firm* — Bookoff McAndrews, PLLC

(57) ABSTRACT

Embodiments of the present disclosure include a medical device including, among other things, an elongated member having a proximal end, a distal end, and at least one channel. A distal portion of the at least one channel may be displaced relative to a longitudinal axis of the elongated.

19 Claims, 4 Drawing Sheets

(56) References Cited

U.S. PATENT DOCUMENTS

| | | | | |
|---|---|---|---|---|
| 2006/0281973 | A1* | 12/2006 | Sugita | A61B 1/0008 600/156 |
| 2007/0066869 | A1* | 3/2007 | Hoffman | A61B 1/00135 600/121 |
| 2007/0177009 | A1* | 8/2007 | Bayer | A61B 1/00096 348/65 |
| 2008/0188868 | A1* | 8/2008 | Weitzner | A61B 1/0014 606/130 |
| 2009/0182198 | A1* | 7/2009 | Skerven | A61B 1/00087 600/121 |
| 2009/0299135 | A1* | 12/2009 | Spivey | A61B 1/00073 600/106 |
| 2010/0160729 | A1* | 6/2010 | Smith | A61B 1/00098 600/114 |
| 2011/0124960 | A1* | 5/2011 | St. Onge | A61B 1/0008 600/104 |
| 2012/0083796 | A1* | 4/2012 | Grover | A61B 17/00234 606/114 |

* cited by examiner

TISSUE RESECTION DEVICE AND RELATED METHODS OF USE

CROSS-REFERENCE TO RELATED APPLICATIONS

This application claims the benefit of priority from U.S. Provisional Application No. 61/658,700 filed on Jun. 12, 2012, the entirety of which is incorporated by reference herein.

FIELD OF THE INVENTION

This disclosure relates generally to devices and methods for resecting tissue. More particularly, embodiments of the disclosure relate to minimally invasive devices and methods for endoscopic mucosal resection and endoscopic submucosal dissection.

BACKGROUND OF THE INVENTION

Organ walls are composed of several layers: the mucosa (the surface layer), the submucosa, the muscularis (muscle layer), and the serosa (connective tissue layer). In gastrointestinal, colonic, and esophageal cancer, for example, small lesions or cancerous masses may form along the mucosa and often extend into the lumens of the organs. Conventionally, that condition is treated by cutting out a portion of the affected organ wall. This procedure, however, may cause discomfort to patients, and pose health risks. Recently, physicians have adopted a minimally invasive technique called endoscopic mucosal resection (EMR), and another called endoscopic submucosal dissection, which removes the cancerous or abnormal tissues (e.g., lesions), keeping the walls intact.

EMR is generally performed with an endoscope, which is a long, narrow elongated member optionally equipped with a light, video camera, and other instruments. During EMR, the endoscope is passed down the throat or guided through the rectum to reach an abnormality such as a lesion in an affected organ. The distal end of the endoscope, further equipped with a cap carrying a small wire loop or a band, is guided towards the lesion. Once there, suction may be applied through a lumen in the elongated member, or some other retraction tool extending from the endoscope is retracted, to draw the lesion towards the endoscope cap. When the lesion is sufficiently drawn into the cap, the wire loop or band closes around the lesion, resecting it from the organ wall, or banding it. Subsequently, the excised tissue may be extracted by e.g., the vacuum, for examination, biopsy, or disposal.

Certain polyps, such as pedunculated polyps, are characterized by a stalk attached to the mucosal layer. Drawing such polyps into the cap, without drawing in any other tissue, is possible. Certain other polyps, such as sessile polyps, however, exhibit a broad base, and lay flat on the mucosal surface, devoid of a stalk. It is often difficult to grasp these polyps, without drawing in a part of the muscularis layer. Conventional EMR caps include axial channels for introducing devices proximate the affected area. Because polyps or lesions are present on the organ walls, it is often difficult to grasp such objects readily with axially extending devices and obtain a better vantage point to apply overhead lifting force.

Therefore, there exists a need for an improved endoscopic mucosal resection tool that aids in grasping and/or resecting both pedunculated and sessile polyps without damaging the surrounding tissue or muscle layers of the organ

SUMMARY OF THE INVENTION

Embodiments of the present disclosure provide a medical device for resecting an undesired mass from a patient's body using a minimally invasive surgical method.

In accordance with an aspect of the present disclosure, embodiments of the present disclosure include a medical device including, among other things, an elongated member having a proximal end, a distal end, and at least one channel extending between the proximal and distal ends. A distal portion of the at least one channel may be displaced relative to a longitudinal axis of the elongated member, and the distal portion of the at least one channel may be defined by a cap secured to the distal end of the elongated member.

In various embodiments, the medical device may include one or more of the following additional features: the cap may be removably coupled to the elongated member; the cap may include a wall having an open section proximal to a distal end of the cap; a distal end of the distal portion of the at least one of the channels may include a notch; the elongated member may include at least one other channel; the cap may include a mating section configured to receive the distal end of the elongated member; the mating section may be configured to frictionally engage the distal end of the elongated member; and a distal portion of the cap may define an opening in the wall proximal to a distalmost end of the cap.

According to another embodiment, a medical device may include, among other things, an elongated member having a proximal end, a distal end, and a channel extending therebetween. The medical device may further include a cap coupled to the distal end of the elongated member, wherein the cap may include a lumen and a diverter tube extending within the lumen from a proximal end portion of the cap, wherein the diverter tube is displaced relative to a longitudinal axis of the elongate member.

In various embodiments, the medical device may include one or more of the following additional features: the diverter tube may include a proximal end having a flared opening in communication with the lumen of the elongated member; the cap may be removably coupled to the distal end of the elongated member; the diverter tube may be in communication with a working channel of the elongated member; a distal portion of the cap may define an extension; the distal end of the diverter tube may include a sidewall having a notch; a portion of the cap may be configured to receive and frictionally engage the distal end of the elongated member; the cap may be integrally formed with the elongate member; and a portion of the diverter tube may be curved.

A further aspect of the present disclosure provides a method for resecting tissue from a patient. The method may include, among other things, inserting a resection device into a body cavity. The resection device may include an elongated member having a proximal end, a distal end, and at least one channel extending between the proximal and distal ends, wherein the distal portion of the at least one channel is disposed in a cap and displaced relative to a longitudinal axis of the elongated member. The method may further include advancing an instrument through the elongated member to excise tissue.

In various embodiments, the method may further include one or more of the following features: the cap may be removably coupled to the elongated member, and the cap may include a proximal portion configured to frictionally receive the distal end of the elongated member; and may include advancing a second instrument through a lumen of the cap.

Additional objects and advantages of the claimed invention will be set forth in part in the description, which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF THE EMBODIMENTS

Figure 1:
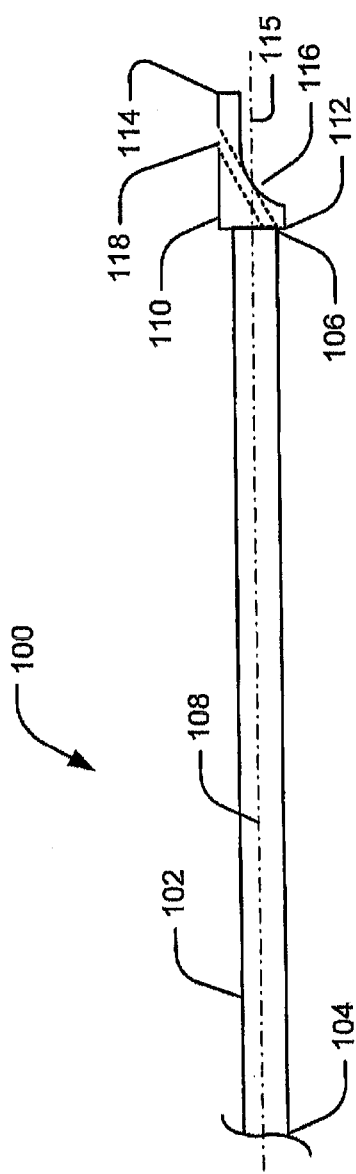
FIG. 1 is a side view of an exemplary endoscopic resection device.

Reference will now be made in detail to embodiments of the present disclosure, an example of which is illustrated in the accompanying drawings. Wherever possible, the same reference numbers will be used throughout the drawings to refer to the same or like parts. The term "distal" refers to the end farthest away from a medical professional when introducing a device in a patient. By contrast, "proximal" refers to the end closest to the medical professional when placing a device in the patient.

Overview

Embodiments of the present disclosure relate to devices and methods for resecting or banding cancerous or otherwise undesirable tissue in a patient's body. For example, the device may be used in a minimally invasive procedure to remove cancerous polyps or lesions from the mucosal walls of the colon, esophagus, stomach, duodenum, or any other suitable location. A physician may also wish to resect tissue to conduct a biopsy or other examination. It should be understood that the resection device may perform the functions of both resecting and retrieving, and banding, or another medical procedure, but for convenience, the term "resection device" will be used throughout this application. "Banding" as used in this disclosure, refers to a medical procedure that uses elastic or ligation bands to capture and visualize tissue before resection with a snare, and to constrict blood supply to lesions, polyps, or organs, so that the ligated tissue eventually dies and sloughs away from the supporting tissue.

For conducting such procedures, embodiments of the resection device described in this disclosure may include an EMR cap assembly coupled to a distal portion of any suitable elongated member or other introduction sheath, such as an endoscope, for ensnaring, banding, cauterizing, and/or extracting tissue, such as a lesion. The cap includes a proximal end, a distal end, and at least one lumen or opening extending through the length of the cap. Cancerous or undesirable tissue may be drawn into or above this lumen for resection. In some embodiments, the lumen may be fully or partially circumferential. Within the lumen, the cap may include a second, smaller diverted lumen that extends substantially diametrically from the proximal end to a distal portion of the cap. This diverted lumen design allows operators to divert medical devices from the original longitudinal axis inside the cap, at a particular preconfigured direction or angle, so that their end-effectors may extend out of the lumen at an angle to the cap's longitudinal axis. The diversion of this diverted lumen may be configured such that the end-effector exits the distal end of the cap at a location where it is positioned to more efficiently grasp and apply tissue tension for resection. In addition, the diverted lumen may include a curvilinear configuration.

In the following sections, embodiments of the present disclosure will be described using an exemplary body organ—the gastrointestinal tract. The embodiments of the resection device aim to grasp and/or remove a lesion on an inner wall of the stomach effectively, without damaging the underlying tissue layers. It will be understood that the stomach is merely exemplary, and that the device may be utilized in any other suitable organ, and in particular, the gastrointestinal tract, such as the colon, duodenum, esophagus, or any other organ that may be subject to polyps, lesions, and the like. Further, the medical device and methods disclosed herein may be utilized in other in any suitable location of a patient's body. Further, the methods and devices disclosed herein may be used for any suitable disease state, including procedures for resection of organs or for general exploration and lifting that does not necessarily include resecting tissue.

Exemplary Embodiments

FIG. 1 is a schematic of an exemplary resection device 100 for resecting polyps, lesions, tissue samples, or other undesired tissue from the interior bodily walls of a patient, according to embodiments of the present disclosure. Resection device 100 includes an elongated member 102 having a proximal end 104, a distal end 106, and a lumen 108 extending between proximal and distal ends 104, 106. Proximal end 104 may be coupled to a handle (not shown), while distal end 106 is coupled to a resection cap 110.

Elongated member 102 may be any flexible or rigid member adapted to be advanced into a patient. Further, elongated member 102 may be flexible in certain portions and rigid in others. For example, the elongated member's distal end 106 may be flexible or steerable, allowing the member to traverse circuitous cavities or lumens, while the rest of the member may be rigid providing sufficient force to urge it distally.

In the illustrated embodiment, elongated member 102 is generally circular, with a generally circular hollow interior lumen 108. Further, elongated member 102 may have a uniform diameter or it may be tapered at the distal end 106 to allow convenient insertion within a patient's body. Depending upon the particular implementation and intended use, the length, configuration, and cross-section of elongated member 102 may vary. In addition, changes in flexibility or rigidity may be effected by changes in material along the length, selective reinforcing of discrete regions by, e.g., coils or braiding within the walls of the member, changes in material properties of the same material and so forth.

Lumen 108 may include one or more channels (not shown). Through these channels, an operator may introduce one or more medical devices to extend out of the distal end 106. For example, during a resection, the operator may introduce a suction device into one channel, and a snare instrument into another. Additionally, from time to time, during a procedure, the operator may insert a light source, a camera, an injector, or a morcellator within the channels. These examples are not limited to the embodiments provided; any medical device of proper dimensions and design may be utilized. Because different devices may be inserted in the elongated member 102, the dimensions of its channels may not be uniform. Some channels may have a larger diameter, while others may have a smaller diameter. The channels may have any cross-sectional geometry, including, but not limited to, circular, square, triangular, or polygonal. Further, some channels may include permanently fixed medical devices, such as light sources or cameras, while other channels may allow insertion of exchangeable medical devices, as the operator desires.

Lubricious materials and antibacterial agents may coat elongated member 102 for easy insertion into tight cavities and for preventing infections, respectively. Further, portions of elongated member 102 may include radiopaque materials to visualize the position of elongated member 102 within a patient's body. Elongated member 102 described here may be any well-known endoscopic device used for medical procedures, including colonoscopy, resectoscopy, cholangioscopy, or mucosal resection, and thus, this device will not be discussed in detail in the remainder of the disclosure.

Cap 110 may be a generally tubular elongated member configured to fit over the elongated member's distal end 106. Alternatively, cap 110 may be configured to fit into and extend from a lumen of elongated member 102. The cap 110 has a proximal end 112, a distal end 114, and a lumen 116 extending from the cap's proximal end 112 to the cap's distal end 114. Further, cap 110 includes a diverter tube 118 (shown in FIG. 1 with dashed lines) within lumen 116, attached to the cap's proximal end 112, which may be formed as a curve, and diverting the instrument from the longitudinal axis 115. Although a tube is illustrated, any structure can be used that provides a channel for a medical device.

The diverter tube 118 provides a diverted path for medical resection devices, such as snare loops, ligation bands, suction devices, graspers, etc., to effectively grasp and resect lesions from within a patient's body. The diverter tube 118 provides a channel diverted away from the origin axis for the medical devices, allowing them to exit the cap's distal end 114 at an angle to the longitudinal axis 115. Such positioning may place the end-effectors of medical devices at a position relative to the cap's distal end 114 and origin axis, giving the devices a better vantage point to approach desired tissue to facilitate lifting or resecting of tissue.

Cap 110 may be temporarily or permanently attached to the elongated member's distal end 106. Temporary attachment allows operators to fix cap 110 at the distal end of any well-known endoscopic device or catheter. Moreover, detachable caps may be replaced by other end-effectors (including, e.g., other caps) during a procedure, allowing an operator to use the same endoscopic device for different applications. Permanent attachment, alternatively, ensures that cap 110 does not separate from the elongated member's distal end 106 inadvertently during a procedure. Based on the desired application, caps may be manufactured either permanently attached to the distal end of elongated member 102 or with temporary attachment means.

For temporary attachment, the proximal portion of the cap may include an attachment section (which may be substantially cylindrical) that may include threading, projections, grooves, or any other temporary attachment means for attaching the cap to the elongated member. Temporary attachment means (not shown) may include, but are not limited to, friction-fit, screw-fit, luer-lock, snap-fit, or compression fit arrangements. In some embodiments, the attachment section may be adjustable, allowing operators to connect elongated members of varying diameter or designs to the cap. For instance, the attachment section may be formed of a flexible material, such as elastic or rubber, which may expand radially to fit the cap around elongated members with diameters greater than the cap's distal diameter, and return to a relaxed position to fit the cap around an elongated member with a diameter comparable with the cap's diameter. In some embodiments, the attachment section may include bumps, holes, ridges, or grooves to aid in connection. It will be understood that the attachment section may be made of any other material or of any other design to provide adjustability without departing from the scope of the present disclosure.

Permanent attachment may include welding, gluing, soldering, melting, molding, or the cap 110 may be integrally formed with elongated member 102. Other temporary or permanent attachment means may just as well be contemplated without departing from the scope of the present disclosure.

Figure 2:
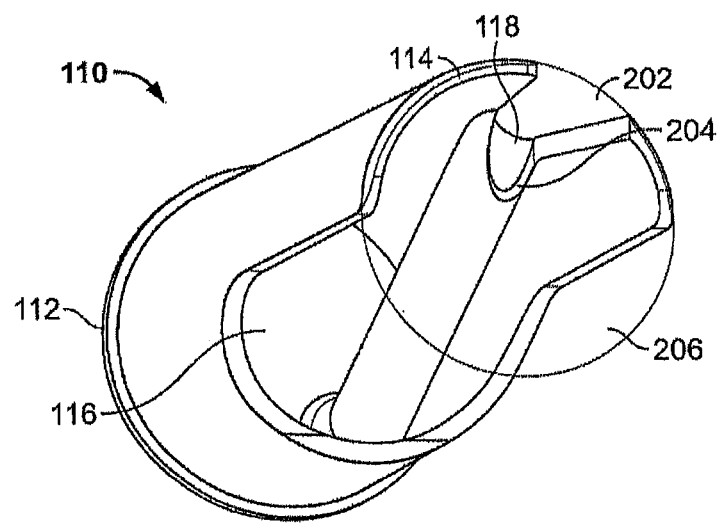
FIG. 2 is a perspective distal end view of an exemplary endoscopic mucosal resection cap according to an embodiment of the present disclosure.

More details of one embodiment of a cap 110 are shown in FIG. 2, which is an end view of the exemplary EMR cap 110. As previously described, cap 110 includes a substantially elongate body extending from proximal end 112 to distal end 114 along longitudinal axis 115, and includes lumen 116 and diverter tube 118. Lumen 116 extends from proximal end 112 to distal end 114 of cap 110, and diverter tube 118 may extend from proximal end 112 to a distal portion of cap 110 or may extend beyond the distal portion of cap 100. The cap 100 may also extend beyond the diverter tube 118 and also may be adapted to hold tissue in a region out of a working area of the elongate member 102.

Cap 110 may include a circular or partially circular cross-section or it may have a cross-section adapted to particular body cavities. Where required by given applications, cap 110 may include, for example, elliptical, semicircular, rhombic, or rectangular profiles. Moreover, the diameter of cap 110 may vary based on the size of the body lumens in which it operates. For example, if cap 110 is inserted through the urethra, its diameter may be very small. Conversely, if cap 110 is inserted through the rectum, its diameter may be larger.

Lumen 116 extends axially along cap 110 and diverter tube 118 extends and diverts at an angle from proximal end 112 to a distal portion at or proximal of distal end 114. For example, diverter tube 118 may run diametrically across the length of cap 110. In some embodiments, diverter tube 118 may be curvilinear. In other embodiments (not shown), diverter tube 118 may begin at a proximal portion of lumen 116, and extend to a distal portion of lumen 116. In such an embodiment, an extension or support member (not shown)

may extend from the inner surface of the cap to support the ends of diverter tube 118. It will be understood that diverter tube 118 may extend at any angle from longitudinal axis 115. For example, the tube may extend at 30 degrees from longitudinal axis 115 or the distal end of diverter tube 118 may be positioned at an angle to the longitudinal axis, but diverter tube 118 may not be straight; it may curve. In all embodiments, however, diverter tube 118 extends from a section of the proximal end of cap 110 to a section of the cap's distal portion, along at least a portion of the length of cap 110. In the illustrated example, the diverter tube 118 begins from the bottom of the proximal rim up to a top distal portion of the cap 110.

In the illustrated embodiments, the angle and distal placement of diverter tube 118 are preconfigured. In other embodiments (not shown), diverter tube 118 may only be fixed at its proximal end, and its distal portion may be free to rotate and alter its angular displacement. Alternatively, the distal end of diverter tube 118 may be fixed and the operator may be able to rotate the proximal end along the cap's proximal end 112 to alter the angle of deviation of diverter tube 118. A rotating or pivoting mechanism (not shown) may be incorporated, depending on the case, to modify the deviation of diverter tube 118 as and when required.

Diverter tube 118 may extend until the cap's distal end 114, such that a medical device present in diverter tube 118 exits from distal end 114 at a particular angle. In other embodiments, diverter tube 118 may not extend up to the distal end 114, but instead may extend only up to a distal portion of cap 110 proximal to the distal end 114. In such an instance, an exit aperture 202 (shown in FIG. 2) may be structured along a wall of the cap 110 to allow a medical device to exit the tube at the distal end. Aperture 202 may be circular, and similar in dimensions to the distal opening of diverter tube 118. Alternatively, as illustrated in FIG. 2, aperture 202 comprises of a slot that extends from the distal end of diverter tube 118 to the cap's distal end 114. Here, the sides of aperture 202 extend in parallel upwards from the tube's distal end to the cap's distal end 114; but in other embodiments, the slot's shape may considerably vary without departing from the scope of the present disclosure. An extending aperture 202 may be especially useful in instances when it is advantageous to grasp or secure tissue within the vicinity of the cap or even proximal to the distal end of the cap. It can also be appreciated that the diverter tube 118 could end beyond or flush with the distal end of the cap and allow the medical device to pivot back toward the cap 110.

The distal end of the diverter tube 118 may further include a notch 204 (shown in FIG. 2). The notch improves the ability of the medical device to exit the diverter tube and enter the lumen 116 at an angle. For example, with notch 204 in place, the medical device exiting diverter tube 118 may not exit from aperture 202. Instead, the medical device may exit through notch 204 and enter lumen 116. Because of the notch, however, the medical device exits diverter tube 118 at an angle inclined towards the central axis and not parallel to the central axis. In some embodiments, the medical device may exit diverter tube 118 parallel to the central axis. The size and depth of notch 204 may differ, varying the angle of approach of the medical device exiting the diverter tube 118.

The outer surface of cap 110 may be uniformly cylindrical along its length, distally flaring, or distally tapering, without departing from the scope of the present disclosure. Lumen 116 forms a cavity that can receive tissue for resection. Further, cap 110 may be a complete cylindrical structure with a proximal and distal opening, or it may be shaped as an incomplete cylinder along all or a portion of its axis having one or more open sections 206 in the wall of the cylinder, as illustrated in FIGS. 1 to 5. Here, one open section 206 may extend partially along the circumference of cap 110 from distal end 114 to a proximal portion of cap 110, forming a hood along a portion of cap 110. In this case, the remaining cap portion may be a little more than half of a cylinder. Open section 206 may be present on the surface of cap 110 that is opposite the distal end of diverter tube 118. Through such a cutout, lumen 116 may contact the lesion at an angle, rather than only at the distal end of the medical device. Moreover, with such an arrangement, resection device 100 may not require to draw the lesion into lumen 116. Instead, the lesion may be situated within the channel when cap 110 is placed over the lesion at an angle.

It will be understood that open section 206 may be larger or smaller without departing from the scope of the present disclosure. For example, open section 206 may only extend from the distal end 114 to a portion proximal along the cap's length. Alternatively, open section 206 may extend along the entire length of cap 110, leaving a portion of the cap and a rim at proximal end 112 for attachment to elongated member 102. Moreover, the shape of open section 206 may vary from application to application. In some instances, it may be substantially rectangular; in others, it may be for example, circular, oval, elliptical, or triangular.

Figure 3:
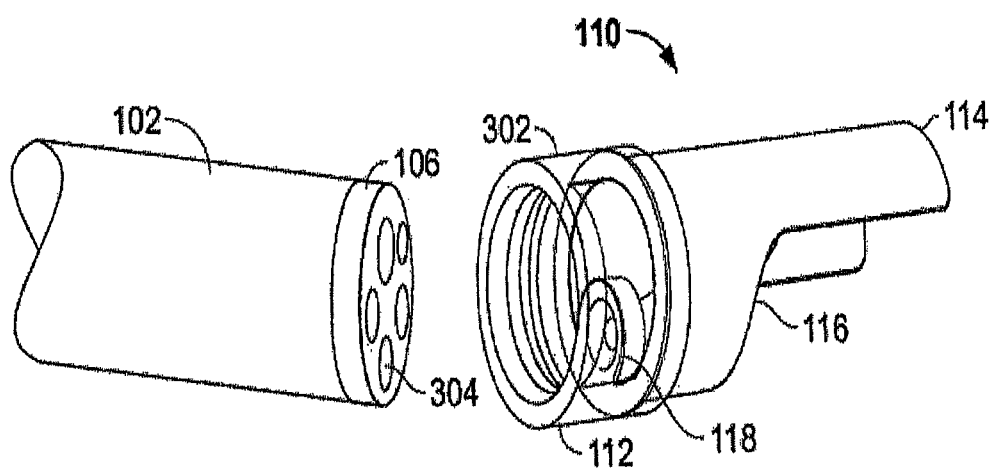
FIG. 3 is a schematic view of an exemplary elongate member and the endoscopic mucosal resection cap of FIG. 2.

FIG. 3 illustrates the cap 110 in position for attachment with the elongated member 102. Here, the cap's proximal end 112 includes an attachment member 302 that is adapted to fit or engage with the elongated member's distal end 106. In the illustrated embodiment, the attachment member 302 includes compressive rings to engage the distal end of the elongated member 102. It will be understood, however, that these rings may just as easily be replaced by screw threads, snap-fit projections, ribs, taper locks or grooves, or any other attachment means. The figure further illustrates multiple working channels 304 of the elongate member. In some embodiments, member 102 may include a matching component to a ring, ridge, notch, tab, or bump on the cap 110.

Figure 4A:
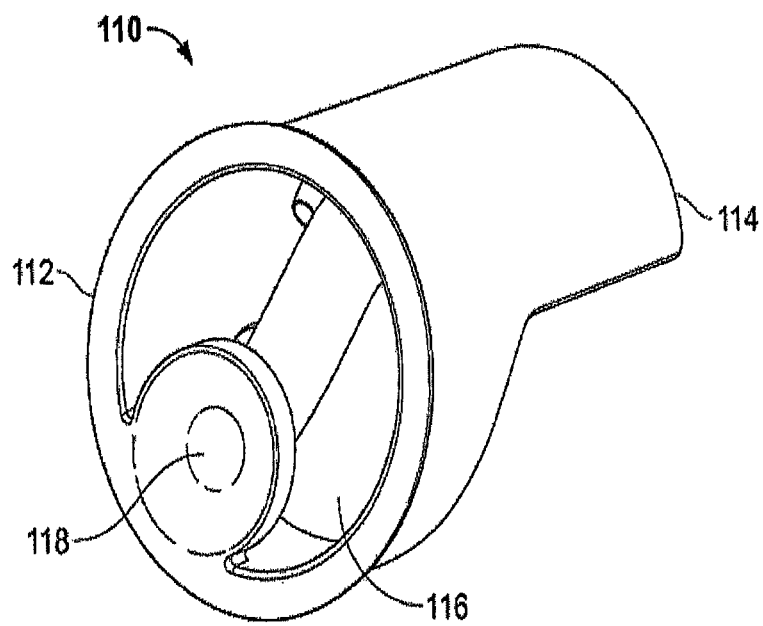
FIG. 4A is a perspective proximal end view of another embodiment of an endoscopic mucosal resection cap.
Figure 4B:
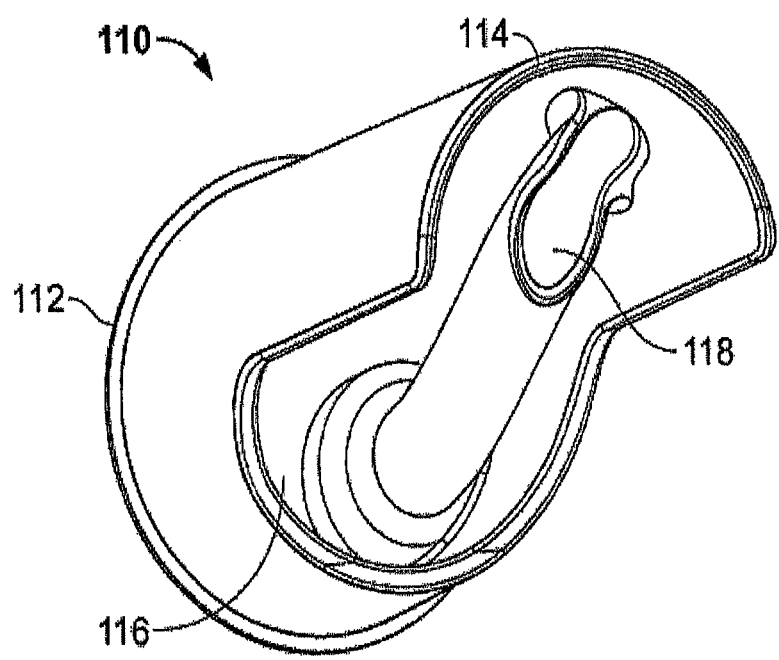
FIG. 4B is a perspective end view of the embodiment shown in FIG. 4A.

The engagement of elongated member 102 and cap 110 are such that at least one working channel 304 of elongated member 102 is aligned with the proximal opening of diverter tube 118. In one alignment technique, the proximal end of the diverter tube 118 is enlarged or flared such that more surface area is available for alignment. FIGS. 4A and 4B, which are schematic end views (proximal and distal, respectively) of cap 110, illustrate such an embodiment.

Various other alignment techniques (not shown) may be implemented. For instance, the attachment feature between elongated member 102 and cap 110 may be such that in the locked position, a channel in the elongate member 102 and diverter tube 118 align. For example, a screw-fit or taper-lock arrangement may ensure that, when fully screwed or locked, the two channels align. Similarly, for snap-fit arrangements, a small projection and groove assembly may be incorporated in the coupling surfaces of elongated member 102 and cap 110 perpendicular to the snap-fit projection-groove assembly. The operator may rotate cap 110 until the projection mates the groove. Any other mating feature, such as indicators at the outer surface, may be just as easily introduced without departing from the scope of the present disclosure. Alternatively, an alignment tool may be supplied to ensure alignment. In some embodiments, diverter tube 118 may extend proximally beyond the proximal edge of the cap 110. This extension may be inserted into a working channel, such as channel 304, upon assembly. The proximal edge of an extension may be tapered to avoid interference with a medical device inserted into tube 118. Alternatively, the cap 110 and the elongate member 102 may have external indicia which align when cap 110 is in place to align the diverter tube 118 with a channel.

In some instances, such as the embodiment illustrated in FIG. 3, the elongated member 102 may have multiple working channels 304. During the course of a procedure, the operator may wish to insert different medical devices in diverted tube 118. In such an embodiment, all the working channels 304 may be aligned with the diverted tube. For example, instead of one groove-projection assembly, the elongate member-cap junction may have multiple groove-projection assemblies—each corresponding to the alignment of a different working channel with the diverted tube. Similarly, in case of indicators, multiple indicators may be marked along the elongate member-cap junction, each indicating the alignment of a different channel 304 with diverted tube 118. With such an alignment mechanism in place, operators may selectively rotate the EMR cap 110 with respect to the elongate member to select alignment between a particular working channel 304 and diverter tube 118.

Further, the edges of cap 110 may be beveled or smoothened such that cap 110 is atraumatic to the surrounding tissue. Moreover, to inhibit bacterial growth in the body cavity or in the mucosal wall, cap 110 may be coated with an antibacterial coating. The coating may contain an inorganic antibiotic agent, disposed in a polymeric matrix, which adheres the antibiotic agent to the cap's surface. Further, a drug releasing coating may also be applied to the outer surface of cap 110, assisting in healing.

Any suitable material may form cap 110. Such materials may include those mentioned above. For instance, rigid or semi-rigid materials such as metals (including shape-memory materials such as nitinol), polymers, resins, or plastics may be used. Cap 110 may also be optically transparent or translucent, allowing physicians to visualize the lesion being resected. Further, a biocompatible material that does not irritate the body lumens may be applied as a coating over the outer surface of cap 110. Moreover, a coating may be applied to a cap to prevent biofluids from adhering to the transparent surface of the cap to maintain visualization thru the cap.

Figure 5A:
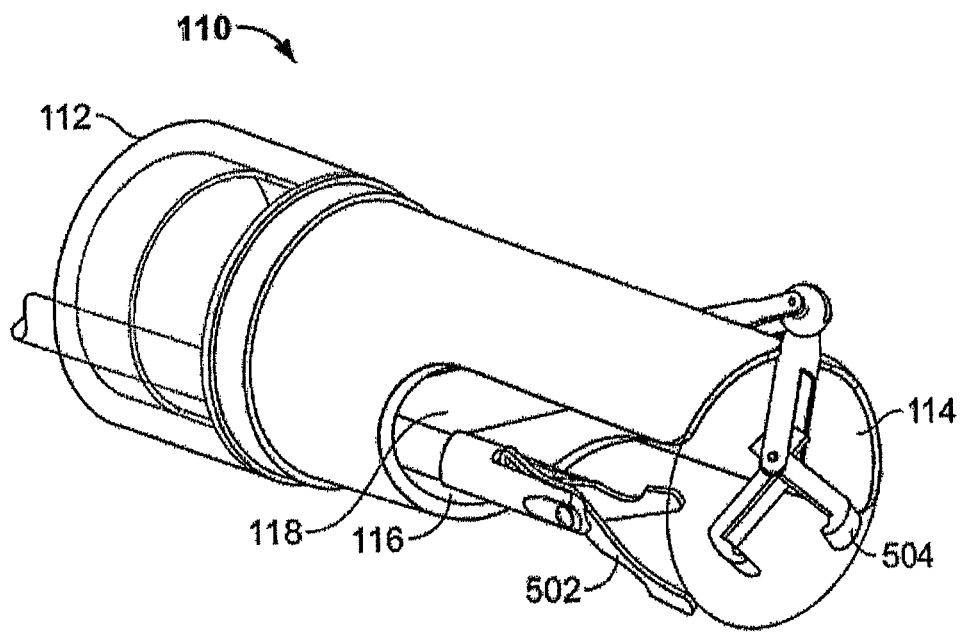
FIGS. 5A and 5B are schematic distal end views of the exemplary cap of FIG. 2 in situ within a patient's body.
Figure 5B:
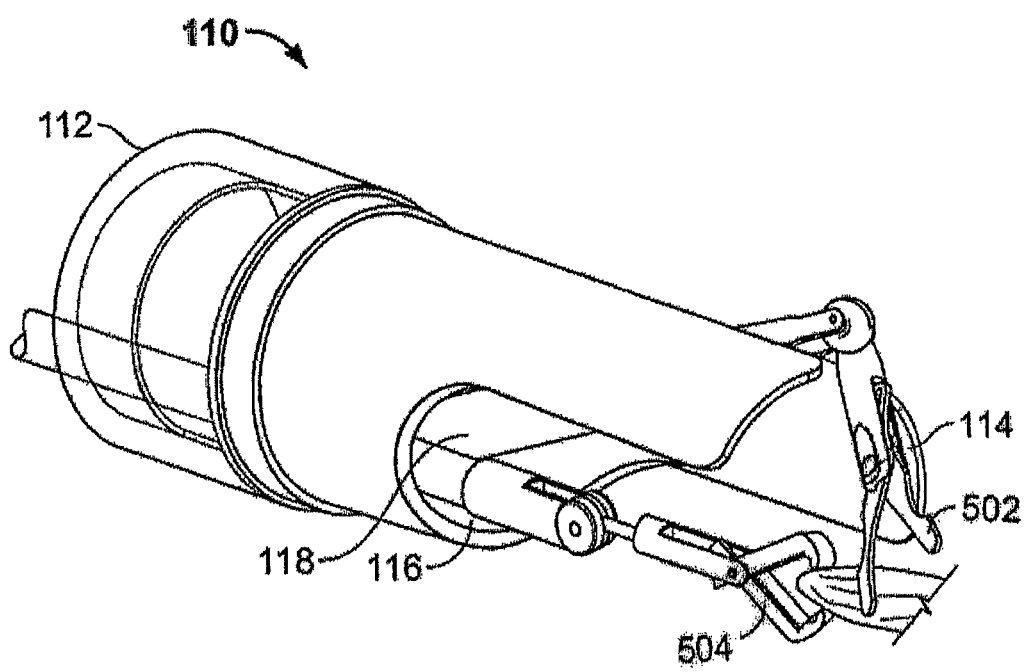

In use, as shown in, e.g., FIGS. 5A-5B, the resection device 100 may be advanced to a location proximate targeted tissue, e.g., a lesion located above the muscularis layer. A grasper 504 may be provided through diverter tube 118 to acquire the targeted tissue. Subsequently, a resecting device 502, e.g., a scissor, probe, knife, snare, needle or hook powered or non-powered by RF, laser, ultrasonics, waterjet or other energy source, may be introduced through lumen 116 to sever or approximate the targeted tissue. Alternatively, the grasper 504 may be provided through lumen 116 and the resecting device 502 may be introduced through diverter tube 118. In other embodiments, the cap may include multiple diverter tubes and both the grasper 504 and the resecting tools may be introduced in the diverter tubes. Further, other medical devices may also be introduced through the diverter tubes without departing from the scope of the present disclosure. Because the grasper 504 exits diverter tube 118 at an angle, it may be configured such that the distal end of the grasper 504 is positioned at an angle to the cap's distal end 114. Such positioning enables the grasper 504 to easily approach and acquire the targeted tissue. Moreover, with this arrangement, saline injections may not be required to lift the lesion off the muscularis. Additionally, any working channel may be configured to pull a vacuum on tissue. If the cap has a side opening, tissue may be pulled into the cap to assist in resection.

In other embodiments, the resecting means of the device may be positioned at an angle, including, but not limited to, an acute angle to the distal end of cap 110, to better cauterize the underlying undesired tissue.

The following section sets out an exemplary method for resecting lesions, lesions, or any other tissue from a patient's body. A typical location for a resection of this sort is the stomach, and that location will be discussed here. As will be understood by those in the art, other patient locations would be equally suitable. Either a percutaneous incision is made to access the gastrointestinal tract, or the resection device 100 may be inserted through a natural opening, such as the mouth.

Once inserted, the resection device 100 is directed towards, e.g., a lesion present on mucosal walls. FIGS. 5A and 5B are schematic views illustrating cap 110 present within a patient's body, proximal a lesion site. In FIG. 5A, cap 110 includes a grasper 504 extending through diverter tube 118 and a resecting or ligating device 502 such as an ensnaring, resecting, or banding device in lumen 116. Those of ordinary skill in the art will recognize that the grasper 504 may be inserted through the lumen 116 and the resecting/ligating device 502 may be inserted through the diverter tube 118, as shown in FIG. 5B. A distal portion of the grasper 504, as depicted in FIG. 5A, may include a pivot mechanism or any other steering mechanism that allows the distal end of the grasper 504 to pivot inward toward cap 110 at approximately 90° to diverter tube 118. It will be understood that the pivoting angle may be altered as desired by the operator for effectively grasping and ensnaring lesions. Similarly, in the embodiment of FIG. 5B, the resecting device 502 may include a suitable pivoting or articulating mechanism.

A steering mechanism may be incorporated in resection device 100 (with controls in the handle) to guide and urge the device within a body cavity. A light source and a camera (not shown) may be inserted in the elongate member's lumen 108 to direct device 100 within the stomach, and to identify lesions. Various identification techniques may be employed. For example, a biomarker or dye may be sprayed around the gastrointestinal tract. Cancerous lesions emit a different wavelength when light falls on them, allowing operators to easily detect them.

The grasping device 504, such as suction pump, graspers, forceps, pincers, or any other such medical device that can draw the lesion into the lumen of cap 110, is introduced into lumen 116. Subsequently, the suction device may be powered off or removed, and a telescope or microscope (not shown) may be introduced into the elongated member 102, along with a light device (not shown), allowing a physician to closely examine the lesion, and to determine whether the lesion requires resection. Various other known techniques may be employed for this determination, without departing from the scope of the present disclosure.

For example, when a cancerous lesion is discerned, the cap 110 may be positioned proximate the lesion, and the resecting device 502, such as a knife, needle, snare loop, elastic band, or clipper may be inserted into the device 100, and urged distally into diverter tube 118. The distal end of resecting device 502 may extend beyond the distal end of diverter tube 118, and be positioned substantially parallel to the distal opening of the cap 110. In such a position, when the lesion is drawn into cap 110, resecting device 502, in the deployed state, may be placed substantially parallel to the distal end 114 of cap 110, and therefore, be in a better position to grasp the lesion near its base than a conventional axially extending medical device. The resecting device 502 may subsequently resect the tissue.

FIG. 5B depicts an alternate embodiment, where the resecting device 502 may extend into the diverted tube 118 and the grasping device 504 may be present in lumen 116.

Once the lesion is resected, device 100 may carry out any number of procedures to excise the resected matter. For example, resection device 100 may extract the lesion or morcellate it and then extract it. For extraction, any retrieval device presently known or later developed may be employed. In one embodiment, the lesion may be extracted with the help of suction force applied at proximal end 104 of resection device 100. In another embodiment, a basket, a grasper, or pincers may be used.

Embodiments of the present disclosure may be used in any medical or non-medical procedure, including any medical procedure where appropriate resection of an undesired body tissue is required. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the invention being indicated by the following claims.

What is claimed is:

1. A medical device comprising:
   a tubular member having a proximal end, a distal end, and a channel extending between the proximal and distal ends, wherein a distal portion of the channel is displaced relative to a central longitudinal axis of the tubular member, wherein the distal portion of the channel is defined by a cap secured to the distal end of the tubular member, wherein the distal portion of the channel is housed within a lumen of the cap, wherein a position of the distal portion of the channel does not change relative to the lumen, wherein the lumen has a greater cross-sectional dimension than a cross-sectional dimension of the distal portion of the channel and the lumen surrounds the distal portion of the channel, wherein the channel crosses the central longitudinal axis of the tubular member between a proximal end of the cap and a distal end of the cap, and wherein a distal-most end of the channel opens through a wall of the cap that defines the lumen.

2. The medical device of claim 1, wherein the cap is removably coupled to the tubular member.

3. The medical device of claim 1, wherein the wall of the cap includes an open section proximal to the distal end of the cap.

4. The medical device of claim 1, wherein a distal end of the distal portion of the channel includes a notch.

5. The medical device of claim 1, wherein the tubular member includes at least one other channel.

6. The medical device of claim 1, wherein the cap includes a mating section configured to receive the distal end of the tubular member.

7. The medical device of claim 6, wherein the mating section is configured to frictionally engage the distal end of the tubular member.

8. A medical device comprising:
   a tubular member having a proximal end, a distal end, and a channel extending there between; and
   a cap coupled to the distal end of the tubular member, wherein the cap defines (a) an interior surface defining a lumen, wherein the lumen extends to a distal-most end of the cap; and (b) a diverter tube fixed in a stationary position relative to the lumen and extending within the lumen from a proximal end portion of the cap, wherein the diverter tube is displaced relative to a longitudinal axis of the tubular member, wherein the diverter tube is spaced apart from the interior surface of the cap between a proximal end of the diverter tube and a distal end of the diverter tube, and wherein the distal end of the diverter tube includes a sidewall having a notch.

9. The medical device of claim 8, wherein the proximal end of the diverter tube has a flared opening in communication with the channel of the tubular member.

10. The medical device of claim 8, where the cap is removably coupled to the distal end of the tubular member.

11. The medical device of claim 10, wherein the diverter tube is in communication with the channel of the tubular member.

12. The medical device of claim 8, wherein a distal portion of the cap defines an extension.

13. The medical device of claim 8, wherein a portion of the cap is configured to receive and frictionally engage the distal end of the tubular member.

14. The medical device of claim 8, wherein the cap is integrally formed with the tubular member.

15. The medical device of claim 8, wherein a portion of the diverter tube is curved.

16. The medical device of claim 8, wherein the diverter tube crosses the longitudinal axis of the tubular member between the distal end of the diverter tube and the proximal end of the diverter tube.

17. A method for resecting tissue from a patient, the method comprising:
   inserting a resection device into a body cavity, the resection device comprising:
      a tubular member having a proximal end, a distal end, and at least one channel extending between the proximal and distal ends, wherein a distal portion of the at least one channel is disposed in a cap and displaced relative to a central longitudinal axis of the tubular member, wherein the cap defines an open lumen extending between a proximal end of the cap and a distal end of the cap, wherein the distal portion of the channel extends within the open lumen, a position of the distal portion of the channel does not change, and the lumen surrounds the distal portion of the channel, wherein the distal portion of the channel crosses the central longitudinal axis of the tubular member between the proximal end of the cap and the distal end of the cap, and wherein a distal-most end of the channel opens through a wall of the cap that defines the open lumen; and
   advancing an instrument through the tubular member and into the distal portion of the at least one channel to excise tissue.

18. The method of claim 17, wherein the cap is removably coupled to the tubular member, and the cap includes a proximal portion configured to frictionally receive the distal end of the tubular member.

19. The method of claim 17, further comprising advancing a second instrument through a lumen of the cap.

* * * * *